US010175230B2

United States Patent
Msika et al.

(10) Patent No.: US 10,175,230 B2
(45) Date of Patent: Jan. 8, 2019

(54) USE OF BIOMARKERS FOR EVALUATING THE EFFECTIVENESS OF ACTIVE INGREDIENTS

(71) Applicant: LABORATOIRES EXPANSCIENCE, Courbevoie (FR)

(72) Inventors: Philippe Msika, Versailles (FR); Caroline Baudouin, Rambouillet (FR); Stephanie Bredif, Chaudon (FR)

(73) Assignee: LABORATOIRES EXPANSCIENCE, Paris la Defense (FR)

( * ) Notice: Subject to any disclaimer, the term of this patent is extended or adjusted under 35 U.S.C. 154(b) by 436 days.

(21) Appl. No.: 14/785,212

(22) PCT Filed: Apr. 22, 2014

(86) PCT No.: PCT/EP2014/058042
§ 371 (c)(1),
(2) Date: Oct. 16, 2015

(87) PCT Pub. No.: WO2014/170495
PCT Pub. Date: Oct. 23, 2014

(65) Prior Publication Data
US 2016/0084822 A1 Mar. 24, 2016

(30) Foreign Application Priority Data
Apr. 19, 2013 (FR) ...................... 13 53632

(51) Int. Cl.
*G01N 33/50* (2006.01)
*G01N 33/68* (2006.01)

(52) U.S. Cl.
CPC ....... *G01N 33/5023* (2013.01); *G01N 33/502* (2013.01); *G01N 33/5044* (2013.01); *G01N 33/6881* (2013.01)

(58) Field of Classification Search
CPC .... A61K 36/54; A61K 2300/00; A61K 31/22; A61K 31/23; A61K 31/232; A61K 31/7012; A61K 31/7024; A61K 45/06; A61K 8/60; A61K 8/97; G01N 33/502; G01N 33/5023; G01N 33/5044; G01N 33/6881; A61Q 17/04; A61Q 19/00; A61Q 19/004; A61Q 19/005; A61Q 19/08; A61Q 19/10; A61Q 5/02; C07C 69/02; C07C 69/52; C07C 69/533; C07C 69/587

See application file for complete search history.

(56) References Cited

U.S. PATENT DOCUMENTS

| | | | |
|---|---|---|---|
| 2005/0191709 A1 | 9/2005 | Hendrix et al. | |
| 2010/0035816 A1 | 2/2010 | Piccirilli et al. | |
| 2011/0262025 A1 | 10/2011 | Jarrold et al. | |
| 2012/0184448 A1 | 7/2012 | Stella et al. | |
| 2015/0374605 A1* | 12/2015 | Msika | A61K 36/54 424/59 |

OTHER PUBLICATIONS

Mosby, "Avocado sugars are effective inducer of cutaneous defensive functions," Journal of the American Academy of Dermatology, vol. 56, No. 2, p. AB84, Feb. 1, 2007.
Bredif et al., "Avocado sugars are effective inducers of cutaneous defensive functions," The Journal of Investigative Dermatology, vol. 126, Suppl. 3, p. 52, Sep. 7, 2006.
Mosby, "Antiitching properties of patented avocado peptides," Journal of the American Academy of Dermatology, vol. 62, No. 3, p. AB54, Mar. 1, 2010.
Rawlings, "Trends in stratum corneum research and the management of dry skin conditions," International Journal of Cosmetic Science, vol. 25, No. 1-2, pp. 63-95, Jan. 1, 2003.
Leclere-Bienfait et al., "Avocado perseose, a biomimetic active ingredient for the protection and accompaniment of infants' skin," Journal of Investigative Dermatology, p. S106, May 1, 2013.
International Search Report issued in application No. PCT/EP2014/058042 dated Oct. 15, 2014.

* cited by examiner

*Primary Examiner* — Lisa J Hobbs
(74) *Attorney, Agent, or Firm* — Potomac Law Group, PLLC

(57) ABSTRACT

The invention relates to a method for evaluating the effectiveness of an active ingredient selected from C7 avocado sugars, also called avocado perseose, for preventing or treating a deficiency of the skin barrier, said method comprising the determination of the level of expression and/or activation of at least one biological marker, where said biological marker is selected from epidermal maturation markers, lipid barrier markers, hydric regulation markers and *stratum granulosum* regulation markers.

22 Claims, 4 Drawing Sheets

USE OF BIOMARKERS FOR EVALUATING THE EFFECTIVENESS OF ACTIVE INGREDIENTS

Figure 1:
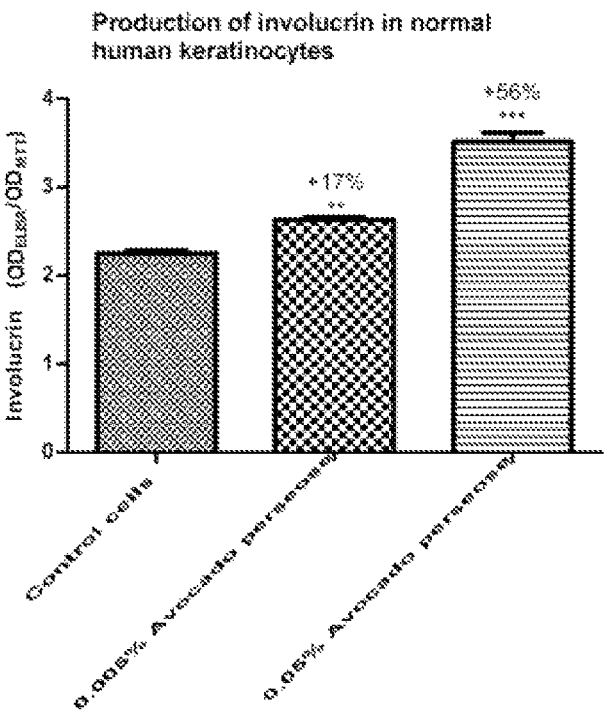

The present invention relates to the field of theranostics, sometimes called theragnostics, i.e., to the evaluation of the effectiveness of active ingredients or compounds in treating subjects, in particular in order to adapt their treatment individually, for personalized medicine. More precisely, the invention belongs to the field of dermatology and relates to methods for evaluating the effectiveness of an active ingredient selected from C7 sugars and derivatives of formula (I), in the prevention and/or treatment of at least one deficiency of the skin barrier of a subject. The skin protects the body from external factors of physical stresses (mechanical factors, thermal factors and UV rays, in particular), chemical stresses (surfactants, extended exposure to water, solvents, etc.) and environmental stresses. Moreover, the skin, as a barrier, protects the body from loss of essential ions, water and serum proteins.

The epidermis constitutes the most superficial layer of the skin and confers the skin with impermeability and resistance to the skin. Four distinct cell layers can be identified in the epidermis, a basal layer (*stratum basalis*), a spinous layer (*stratum spinosum*), a granular layer (*stratum granulosum*), and a horny layer (*stratum corneum*).

In particular, the horny layer (*stratum corneum*) and the granular layer (*stratum granulosum*), i.e., the outermost layers of the skin, provide the barrier function of the skin.

The horny layer is mostly made of cornified keratinocytes, also called corneocytes. Cornified keratinocytes are cells which have lost their cell nucleus due to continuous keratinocyte differentiation, also called keratinocyte maturation or epidermal maturation. Cornified keratinocytes are joined together by desmosomes and organize into a network of joined cells forming flexible and resistant lamellae. Between the cornified keratinocytes the intercellular environment is rich in lipids, in particular those of the family of ceramides. Moreover, the horny layer is home for "natural moisturizing factors" (NMF), which keep the degree of hydration of the skin at an optimal level.

This barrier created by the horny layer is not absolute. Indeed, transepidermal water loss, or insensible water loss, does occur, and although minimal it can increase in certain situations of barrier function deficiency.

The barrier function of the skin changes with the age of the subject and can be incomplete, even deficient, at certain ages of life.

It is known, for example, that the skin of a child is not mature and that its barrier function changes as it matures. In particular, the barrier of a child's skin is only incompletely functional in comparison with adult skin.

For example, Fluhr et al. (*Br J Dermatol* 166 (3): 483-90, 2012) have shown that the water content of the horny layer is lower at birth (newborns 1 to 15 days of age) than during adulthood. Premature infants in particular present increased insensible water loss (insensible water losses are multiplied by about 10 in premature infants) and high sensitivity to infections, testifying to the immaturity of the skin barrier in this subject population.

On the other hand, the skin of older subjects also presents a diminishing of the skin barrier, related to the phenomenon of senescence, also called intrinsic aging (J. Lübbe, *Revue Médicale Suisse*, 62(2472): 488-490, 2004).

The skin barrier can also be weakened as a result of changes in its structure, which may result from endogenous as well as exogenous factors. For example, it is estimated that baby acne, adolescent acne, rosacea or erythrocouperosis, psoriasis, diaper dermatitis, atopic dermatitis, eczema, contact dermatitis, irritant dermatitis and in particular irritant diaper dermatitis or diaper rash, allergic dermatitis, seborrheic dermatitis, dry skin, skin hyperreactivity, to cite only these pathologies, are related to a deficiency of the skin barrier.

Active ingredients for preventing or restoring the barrier function of the skin are already known in the art. In particular, the protective effect on the barrier function of C7 sugars and derivatives thereof, avocado perseose, have already been disclosed (see WO 2005/105123, for example).

However, there has been until now no known biological marker for measuring the effectiveness of said avocado perseose during a treatment, in a particular subject. However, the effectiveness of a dermatological treatment may depend on the condition of the treated subject's skin. As a result, it has been impossible until now to adapt or adjust said treatment according to the treated subject.

The present inventors have, for the first time, identified markers that are specifically expressed or activated when the skin is treated with avocado perseose. They have observed in particular that certain biological markers are expressed more or are more active in skin treated with avocado perseose than in untreated skin. These markers can thus be used to evaluate the effectiveness of avocado perseose in preventing or treating a barrier deficiency in a subject.

DETAILED DESCRIPTION

According to a first aspect, the invention relates to a method for assessing the effectiveness of an active ingredient selected from avocado C7 sugars, designates avocado perseose and which will be defined below, in preventing or treating a deficiency of the skin barrier, said method comprising the determination of the level of expression and/or activation of at least one biological marker.

It is well understood that the active ingredients of the invention are used in mammals, and preferably in humans. More preferably, said compositions are used in children. By "subject" is meant, in the context of the present application, any human subject of any age. Thus, the subject can be, for example, an adult or a child. By "child" is meant according to the invention an individual whose age is below 16 years. Children according to the invention thus encompass newborns, i.e., infants from birth to 1 month of age, nursing infants, i.e., infants between 1 month and 2 years of age, and children 2 years of age or older, i.e., children between 2 and 16 years of age. A "newborn", as defined herein, may be a premature birth or a full-term birth.

To remove any ambiguity, the term "child" used in the present application with no further clarification should be understood in its most general sense, i.e., as referring to a person younger than 16 years of age. Thus, in the context of the present invention, children between 2 and 16 years of age are specifically designated by the expression "children 2 years of age or older."

An "adult" in the context of the present invention is a person who is not a child, i.e., is a person 16 years of age or older. According to a particular embodiment, the subject is a child, preferentially a newborn or a nursing infant.

According to a preferred embodiment, the subject-matter of the invention is a method for assessing the effectiveness of an active ingredient selected from C7 sugars and derivatives of formula (I),

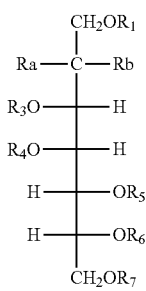

(I)

where
Ra is hydrogen and Rb is —OR2 or CRaRb is the CO radical;
R1, R2, R3, R4, R5, R6 and R7 are, independently from each other:
hydrogen or
a —(CO)—R radical wherein R is a saturated or unsaturated hydrocarbon chain containing from 11 to 24 carbon atoms, optionally substituted by one or more substituents selected from the group consisting of hydroxyl radicals (—OH), ethoxy radicals (—OC2H5) and the —SO3M group with M being hydrogen, an ammonium ion (NH4+) or a metal ion; or
a —(CO)—R' radical wherein R' is a saturated or unsaturated hydrocarbon chain containing from 2 to 10 carbon atoms, optionally substituted by one or more substituents selected from the group consisting of hydroxyl radicals (—OH), ethoxy radicals (—OC2H5) and the —SO3M group with M being hydrogen, an ammonium ion (NH4+) or a metal ion;
in the prevention and/or treatment of at least one deficiency of the skin barrier of a subject, said method comprising the steps of:
a. measuring the level of expression and/or activation of at least one biological marker in a sample of skin cells from the subject, wherein said biological marker is selected from:
  markers of epidermal maturation, said marker of epidermal maturation being preferably selected from desmoglein 1 and involucrin, or;
  markers of the lipid barrier, said marker of the lipid barrier being preferably selected from ceramides, in particular from ceramides 1 to 9, even more particularly ceramide 1, or;
  markers of water regulation, said marker of water regulation being preferably selected from filaggrin, PAD1, hyaluronic acid and transglutaminase 1, or;
  markers of regulation of the *stratum granulosum*, said marker of regulation of the *stratum granulosum* being preferably selected from claudins, in particular claudin 1;
b. measuring the level of expression and/or activation of said biological marker in a reference skin cell sample;
c. comparing the levels of expression and/or activation obtained in step a) with the levels of expression and/or activation obtained in step b);
d. assessing the effectiveness of said active ingredient based on the comparison of step b).

As the skilled person knows well, the barrier function of the skin corresponds to the capacity of the skin to limit exchanges between the external and internal environments of the body, more particularly diffusion of water. The "integrity of the barrier function of the skin" or the "integrity of the skin barrier" (as meant herein, the two expressions are synonymous) thus means that the skin barrier is fully functional, i.e., exchanges, and in particular diffusion of water, are limited.

The integrity of the skin barrier can be assessed by measuring a large number of parameters. In particular, it is common to determine the integrity of the skin barrier by measuring insensible water loss, also called transepidermal water loss. Methods for measuring insensible water loss are well-known to the skilled person and do not need to be described in detail herein (see, for example, H Tagami and K Kikuchi. "Diseases that affect barrier function". In Elias P M and Feingold K R Editors. Skin Barrier. New York: Taylor and Francis; 2005. pp. 447-468). Preferentially, an evaporimeter, which is composed of a probe placed 3 or 6 mm above the skin, is used to measure insensible water loss.

D-mannoheptulose, the first ketoheptose identified in 1916 by La Forge, of general formula (II)

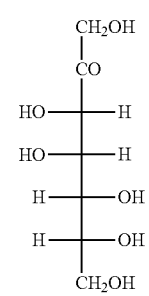

(II)

is a C7 sugar found in certain plants, in particular in alfalfa (*Medicago sativa* L.), in avocado, in fig (*Ficus officinalis* L.), in stonecrop (Sedum *spectabile* Bor.) and in *primula* (*Primula officinalis* Jacq.). However, it is in avocado that the highest concentrations of D-mannoheptulose are found. D-mannoheptulose has already been used in therapeutic applications. For example, patent application WO 95/03809 describes the use of D-mannoheptulose, as glucokinase inhibitor, to inhibit the development of tumor cells, and application US 2003/0092669 describes an oral dietary supplement comprising D-mannoheptulose, which makes it possible to decrease the level of insulin and thus enables weight loss.

Perseitol, the polyol form of D-mannoheptulose, of general formula (III)

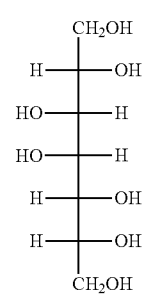

(III)

is also found in avocado, in particular in the fruit or pit of the avocado. It has been shown that perseitol, associated with a potassium ion, inhibits the incorporation of 3H-leucine in Ehrlich ascites carcinoma tumor cells (Shibuya et al., *Pure Appl. Chem.*, 71(6): 1109-1113, 1999).

The use of these sugars (perseitol and D-mannoheptulose) to treat alopecia has already been disclosed (WO 2011/073281). The use of avocado perseose in the treatment of candidiases and pityrosporoses has also already been disclosed (WO 2008/025847). Finally, it has been shown that these sugars could be used to stimulate the synthesis of human beta-defensins (in particular HBD-2) (WO 2005/115421, WO 2005/105123). In particular, these sugars were already known to be effective in the prevention or treatment of pathologies associated with a deficiency of the skin barrier (see WO 2005/105123, for example).

There has been until now no demonstration of biological markers the expression or activation of which has been correlated with the use of these sugars in the treatment of deficiencies of the skin barrier. However, the present inventors have identified such biological markers, making it possible to assess the effectiveness of said sugars in the prevention or treatment of deficiencies of the skin barrier of a subject.

By "effectiveness of an active ingredient in the prevention of at least one deficiency of the skin barrier of a subject" is meant, in the context of the present application, the capacity of said active ingredient to maintain the functional integrity of the skin barrier in the subject. In other words, the effectiveness of an active ingredient in the prevention of at least one deficiency of the skin barrier of a subject corresponds to the capacity of said active ingredient to prevent the deterioration of the barrier function of the skin of said subject.

By "effectiveness of an active ingredient in the treatment of at least one deficiency of the skin barrier of a subject" is meant, in the context of the present application, the capacity of said active ingredient to restore the functional integrity of the skin barrier in the subject. In other words, the effectiveness of an active ingredient in the treatment of at least one deficiency of the skin barrier of a subject corresponds to the capacity of said active ingredient to reverse the deterioration of the barrier function of the skin of said subject. By "biological marker" is meant, in the context of the present application, a feature that is measured objectively and is evaluated as an indicator of normal biological processes, pathogenetic processes, or pharmacological responses to therapeutic interventions. Therefore, biological marker refers to a whole range of various substances and parameters. For example, a biological marker can be a substance the detection of which indicates a particular pathological condition (for example, the presence of activated protein C as a marker of infection) or, conversely, a substance the detection of which indicates a specific physiological state. The biological marker according to the invention is preferentially a gene, products of a gene such as its transcripts and peptides resulting from its transcripts, a lipid, a sugar or a metabolite.

According to an embodiment of the present invention, the biological marker is a gene, gene products such as transcripts or peptides, a lipid, a sugar or a metabolite, the changes in expression of which, in particular the level of expression, correlate with a physiological state of the skin barrier.

According to an embodiment of the present invention, the biological marker is a gene, gene products such as transcripts or peptides, a lipid, a sugar or a metabolite, the changes in activation of which, in particular of level of activation, correlate with a physiological state of the skin barrier. According to a particular embodiment, the biological marker is a peptide having enzymatic activity.

According to the invention, the biological marker is selected from markers of epidermal maturation, markers of the lipid barrier, markers of water regulation, and markers of regulation of the *stratum granulosum*.

The inventors showed in particular that treatment with avocado perseose resulted in an increase in the expression of key markers of epidermal maturation such as desmoglein and involucrin in in vitro skin models.

The protein involucrin is expressed in the horny-granular layers. It is the first precursor of the cornified envelope and accounts for 5-15% thereof, and also serves as a link with the lipid cornified envelope. The protein desmoglein is synthesized by keratinocytes and secreted at the *stratum granulosum-stratum corneum* interface. It is an essential component of corneodesmosomes, the junctions which bind corneocytes.

Measurement of the expression of these markers in a subject treated with the active ingredient of the invention thus makes it possible to measure whether said active ingredient is indeed effective in said subject, in particular on epidermal maturation. Preferentially, the marker of epidermal maturation is selected from desmoglein 1 and involucrin.

In the context of the present invention, the biological marker desmoglein 1 comprises the human DSG1 gene (NCBI reference: GENE ID 1828) and products of this gene. Products of the human DSG1 gene comprise the transcript of the human DSG1 gene and the precursor peptide of human desmoglein 1 protein. In the context of the present invention, the human DSG1 gene transcript is the polypeptide whose sequence is referenced NCBI NM_001942.2. By precursor peptide of human desmoglein 1 protein it is herein referred to the peptide whose peptide sequence is the NCBI reference sequence: NP_001933.2.

In the context of the present invention, the biological marker involucrin comprises the human IVL gene (NCBI reference: Gene ID: 3713) and products of this gene. Products of the human IVL gene comprise the transcript of the human IVL gene and human involucrin protein. In the context of the present invention, the transcript of the human IVL gene is the polypeptide whose sequence is referenced NCBI NM_005547.2. By human involucrin protein it is herein referred to, the protein whose peptide sequence is the NCBI reference sequence: NP_005538.2.

Moreover, the inventors have shown that, in vitro, avocado perseose causes an increase in the expression of ceramides 1 to 9, in particular ceramide 1.

Ceramides are the majority lipids of the lamellar bilayer and are thus very important for the structure and functionality of the *stratum corneum* as a barrier. Ceramide 1, in particular, is underrepresented in dry or aged skin and also in many dermatoses, such as atopic dermatitis, psoriasis, ichthyosis and acne.

Measuring these markers in a subject treated with avocado perseose is thus a simple, solid tool for measuring the effectiveness of the active ingredient, and more particularly the effectiveness of the active ingredient on the maintenance or restoration of the lipid barrier.

Preferentially, the marker of the lipid barrier is selected from ceramides. More preferentially, the marker of the lipid barrier is selected from ceramides 1 to 9. Still more preferentially, the marker of the lipid barrier is ceramide 1.

The protein filaggrin aggregates with cytoskeletal keratin fibers, thus reducing corneocytes to flat discs; this intracellular network confers resistance and protection on the *stratum corneum*. On the other hand, its breakdown leads to the formation of components of natural moisturizing factor (NMF), which is essential for water retention in corneocytes. Filaggrin is broken down by peptidylarginine deiminases (PAD), including peptidylarginine deiminase 1 (PAD1). Hyaluronic acid is found in the epidermis, where it plays a role in the barrier function and in hydration of the horny layer. The enzyme transglutaminase 1 participates in the creation of the cornified envelope by catalyzing the cross-linking of involucrin protein.

The measurement of at least one of these markers can thus be used to evaluate the effectiveness of the active ingredient on water regulation in the horny layer.

Preferentially, the marker of water regulation is selected from filaggrin, peptidylarginine deiminase 1 (PAD1), hyaluronic acid and transglutaminase 1. In the context of the present invention, the biological marker filaggrin comprises the human FLG gene (NCBI reference: Gene ID: 2312) and products of this gene. Products of the human FLG gene comprise the transcript of the human FLG gene and human filaggrin protein. In the context of the present invention, the transcript of the human FLG gene is the polypeptide whose sequence is referenced NCBI NM_002016.1. By human filaggrin it is herein referred to the protein whose peptide sequence is the NCBI reference sequence: NP_002007.1.

In the context of the present invention, the biological marker PAD1 comprises the human PADI1 gene (NCBI reference: Gene ID: 29943) and products of this gene. Products of the human PADI1 gene comprise the transcript of the human PADI1 gene and human "peptidylarginine deiminase 1" protein, hereafter called human PAD1 protein. In the context of the present invention, the transcript of the human PADI1 gene is the polypeptide whose sequence is referenced NCBI NM_013358.2. By human PAD1 protein it is herein referred to the protein whose peptide sequence is the NCBI reference sequence: NP_037490.2.

In the context of the present invention, the biological marker transglutaminase 1 comprises the human TGM1 gene (NCBI reference: Gene ID: 7051) and products of this gene. Products of the human TGM1 gene comprise the transcript of the human TGM1 gene and human transglutaminase 1 protein. In the context of the present invention, the transcript of the human TGM1 gene is the polypeptide whose sequence is referenced NCBI NM_000359.2. By human transglutaminase 1 protein it is herein referred to the protein whose peptide sequence is the NCBI reference sequence: NP_000350.1.

Moreover, it is known that the *stratum granulosum* has a role in the proper functioning of the *stratum corneum*, and thus participates in the barrier function. The inventors have shown that, surprisingly, avocado perseose makes it possible, in vitro, to increase the expression of claudin 1 protein. Claudin 1 is a protein with four transmembrane domains belonging to a family of 24 members. It is a constituent of the tight junctions of the *stratum granulosum*, which form a selective barrier controlling paracellular transport of molecules and inflammatory cells. These tight junctions are also essential to limiting water loss.

Thus, by measuring the level of expression of the markers of regulation of the *stratum granulosum*, it is possible to evaluate or verify the effectiveness of avocado perseose on a particular subject.

Preferentially, the marker of regulation of the *stratum granulosum* is selected from claudins. More preferentially, the marker of regulation of the *stratum granulosum* is claudin 1.

In the context of the present invention, the biological marker claudin 1 comprises the human CLDN1 (NCBI reference: Gene ID: 9076) and products of this gene. Products of the human CLDN1 gene comprise the transcript of the human CLDN1 gene and human claudin 1 protein. In the context of the present invention, the transcript of the human CLDN1 gene is the polypeptide whose sequence is referenced NCBI NM_021101.4. By human claudin 1 protein, it is herein referred to the protein whose peptide sequence is the NCBI reference sequence: NP_066924.1.

The skilled person seeking to determine to which class a gene or protein marker belongs can easily to consult the relevant scientific literature or refer to public databases such as, for example, those found on the website of the National Center for Biotechnology Information (http://www.ncbi.nlm.nih.gov/guide/).

According to a particular embodiment, step a) comprises measurement of the level of expression and/or activation of a combination of biological markers starting from a sample of skin cells from the subject, wherein said combination of markers comprises:
- at least one marker of epidermal maturation, said marker of epidermal maturation being preferably selected from desmoglein 1 and involucrin;
- at least one marker of the lipid barrier, said marker of the lipid barrier being preferably selected from ceramides, in particular from ceramides 1 to 9, even more particularly ceramide 1; and
- at least one marker of water regulation, said marker of water regulation being preferably selected from filaggrin, PAD1, hyaluronic acid and transglutaminase 1;
- at least one marker of regulation of the *stratum granulosum*, said marker of regulation of the *stratum granulosum* being preferably selected from claudins, in particular claudin 1.

Preferentially, the combination of biological markers consists of desmoglein 1, involucrin, ceramide 1, filaggrin, PAD1, hyaluronic acid, transglutaminase 1 and claudin 1.

When the biological marker is a gene, the terms "level of expression of the biological marker" refer to the level of synthesis of the products of this gene. More precisely, when the biological marker is a gene, the level of expression of said biological marker corresponds to the quantity or concentration of the transcripts of said gene and/or the various isoforms of the proteins resulting from said transcripts in the sample.

When the biological marker is a lipid, a sugar or a metabolite, the terms "level of expression of the biological marker" refer to the level of synthesis of said lipid, said sugar or said metabolite. More precisely, when the biological marker is a lipid, a sugar or a metabolite, the level of expression of said biological marker corresponds to the quantity or concentration of said lipid, said sugar or said metabolite in the sample.

The terms "level of activation of the biological marker" apply to biological markers for which a biological activity, in particular an enzyme activity, can be measured. The skilled person knows, for example, that certain peptides have enzymatic activity. The skilled person seeking to determine whether a biological marker of interest has an activity, in particular enzymatic, will easily be able to consult the relevant scientific literature or to refer to public databases such as, for example, those found on the ExPASy website, which indexes enzymes in particular (http://enzyme.expasy.org). According to the invention, the markers PAD1 and transglutaminase 1 are biological markers for which an enzyme activity can be measured.

When the biological marker is a biological marker for which an enzyme activity can be measured, the terms "level of activation of the biological marker" refer to the level of enzymatic activity of said marker. In the context of the present invention, the enzymatic activity of said marker corresponds to the quantity of substrate of said marker catalyzed per unit time by a defined quantum of enzyme. The unit of enzymatic activity U is traditionally expressed in µmol/min or in katals (mol/s). The unit of enzymatic activity U can also be expressed in mg/min when the substrate of the enzyme exists in the body in polymer form, such as is the case, for example, when the substrate is selected from sugars or glycosaminoglycans.

By "measurement of the level of expression and/or activation of a combination of biological markers" it is herein referred to the measurement of the level of expression and/or activation of each marker of the combination.

The expression of a gene can be measured, for example, at the nucleotide level, by measuring the quantity of transcripts of said gene and variants thereof, and can also be measured, for example, at the protein level, by measuring, for example, the amount of one or more isoforms of proteins resulting from said transcripts, and variants thereof.

Thus, by "measurement of the level of expression of said gene" it is herein referred to the measurement of the amount of the gene product in its peptide and/or nucleotide form.

By "desmoglein 1 in its peptide form" it is herein referred to a peptide whose peptide sequence comprises the peptide sequence of human desmoglein 1 protein (whose coding sequence is referenced CCDS11896.1) and/or the precursor peptide thereof. By "precursor peptide of human desmoglein 1 protein", it is herein referred to human desmoglein 1 preproprotein (NCBI reference: NP_001933.2).

By "desmoglein 1 in its nucleotide form" it is herein referred to at least one polynucleotide whose sequence comprises the sequence of the transcript of the human DSG1 gene (NCBI reference: GENE ID 1828). In the context of the present invention, the human DSG1 gene transcript is the polypeptide whose sequence is referenced NCBI NM_001942.2.

By "involucrin in its peptide form" it is herein referred to a peptide whose peptide sequence comprises the peptide sequence of human involucrin protein (NCBI reference: NP_005538.2).

By "involucrin in its nucleotide form" it is herein referred to at least one polynucleotide whose sequence comprises the sequence of the transcript of the human IVL gene (NCBI reference: Gene ID: 3713). In the context of the present invention, the transcript of the human IVL gene is the polypeptide whose sequence is referenced NCBI NM_005547.2.

By "filaggrin in its peptide form" it is herein referred to a peptide whose peptide sequence comprises the peptide sequence of human filaggrin protein (NCBI reference: NP_002007.1).

By "filaggrin in its nucleotide form" it is herein referred to at least one polynucleotide whose sequence comprises the sequence of the transcript of the human FLG gene (NCBI reference: Gene ID: 2312). In the context of the present invention, the transcript of the human FLG gene is the polypeptide whose sequence is referenced NCBI NM_002016.1.

By "PAD1 in its peptide form" it is herein referred to a peptide whose peptide sequence comprises the peptide sequence of the human protein (reference NP_037490.2).

By "PAD1 in its nucleotide form" it is herein referred to at least one polynucleotide whose sequence comprises the sequence of the transcript of the human PADI1 gene (NCBI reference: Gene ID: 29943). In the context of the present invention, the transcript of the human PADI1 gene is the polypeptide whose sequence is referenced NCBI NM_013358.2.

By "transglutaminase 1 in its peptide form" is meant, according to the invention, a peptide whose peptide sequence comprises the peptide sequence of human transglutaminase 1 protein (NCBI reference: NP_000350.1).

By "transglutaminase 1 in its nucleotide form" it is herein referred to at least one polynucleotide whose sequence comprises the sequence of the transcript of the human TGM1 gene (NCBI reference: Gene ID: 7051). In the context of the present invention, the transcript of the human TGM1 gene is the polypeptide whose sequence is referenced NCBI NM_000359.2.

By "claudin 1 in its peptide form" it is herein referred to a peptide whose peptide sequence comprises the peptide sequence of human claudin 1 protein (NCBI reference: NP_066924.1).

By "claudin 1 in its nucleotide form" it is herein referred to at least one polynucleotide whose sequence comprises the sequence of the transcript of the human CLDN1 gene (NCBI reference: Gene ID: 9076). In the context of the present invention, the transcript of the human CLDN1 gene is the polypeptide whose sequence is referenced NCBI NM_021101.4.

According to a preferred embodiment of the invention, the level of expression of the marker selected from desmoglein 1, involucrin or filaggrin corresponds to the level of expression of said marker in its peptide form.

According to a preferred embodiment of the invention, the level of expression of PAD1 corresponds to the level of expression of said marker in its nucleotide form.

Generally, the measurement of the level of expression and/or activation of the biological marker according to the invention will be detected in vitro starting from a sample of skin cells from the subject.

By "sample of skin cells from the subject" it is herein referred to any sample containing skin cells obtained from the subject. Samples of skin cells according to the invention thus comprise fresh skin explants obtained directly from the subject as well as skin cell suspension cultures, skin cell monolayer cultures, skin cell bilayer cultures and tissue models, cultures of reconstructed skin and cultures of reconstructed mucous membranes. Since it is often difficult to work on fresh explants, it is particularly advantageous, in the context of the present invention, to use cultures of skin cells.

Advantageously, the skin cells according to the invention comprise normal cells, healthy or pathological, or cells arising from cell lines. For example, cultured skin cells can be cells obtained from a skin tissue explant. By "explant" or "skin explant" is meant herein a sample of skin cells or tissue, which can be taken for purposes of surgery or in order to perform analyses.

In particular, an explant can be obtained during a surgical exeresis. By "exeresis" is meant herein a surgical procedure consisting in cutting out (excising) a more or less wide or deep part of the skin in order to treat an anomaly or excrescence. Exeresis is performed either to remove a known or suspected cancer tumor, or to treat a benign but troublesome anomaly of the skin, or for functional or esthetic reasons. Exeresis in the context of the invention includes, for example, skin samples obtained after plastic surgery (mammoplasty, abdominoplasty, face-lift, foreskin removal, otoplasty, i.e., reattachment of the ear, syndactyly or supernumerary fingers, etc.).

An explant can also be obtained by biopsy. By "biopsy" is meant herein a sample of skin cells or tissue taken for purposes of analysis. Several types of biopsy procedures are known and practiced in the field. The most common types comprise (1) incisional biopsy, wherein only a sample of tissue is taken; (2) excisional biopsy (or surgical biopsy) which consists of the total ablation of a tumor mass, thus being a therapeutic and diagnostic act, and (3) needle biopsy, wherein a tissue sample is taken with a needle, said needle being large or fine. Other types of biopsy exist, such as, for example, smear or scraping, and are also encompassed in the present invention.

The skin cells according to the invention comprise at least one type of cells typically present in the hypodermis, dermis and/or epidermis. These cells thus comprise, inter alia, keratinocytes, melanocytes, fibroblasts, adipocytes, endothelial cells, mast cells, Langerhans cells and/or Merkel cells. Preferably, the skin cells according to the invention comprise at least keratinocytes and/or fibroblasts. More preferably manner, the skin cells according to the invention comprise keratinocytes and/or fibroblasts. It may be advantageous for the skilled person to assess the effectiveness of active ingredients on the subject's cells subjected to certain stresses, such as, for example, the parts of the subject's skin subjected to sun exposure, or more generally, to UV irradiation. According to an embodiment of the invention, the sample of skin cells comprises cells having been irradiated, preferentially by UV rays.

According to the invention, the sample of skin cells may be treated prior to measurement of the expression of the biological marker, for example in order to extract from said sample of skin cells a sample of mRNA or a sample of protein. The sample of mRNA or of protein may then be used directly to measure the expression of the marker. The preparation and extraction of mRNA and proteins from a cell or tissue sample are routine procedures well-known to the skilled person.

For each type of biological markers of the invention, many methods may be used by the skilled person for measuring the level of expression and/or activation of said biological marker.

When the biological marker is a gene, and the level of expression of the marker is measured on the nucleotide level, i.e., by measuring the quantity of the gene product in its nucleotide form, any technology commonly used by the skilled person can be implemented. Methods for analyzing the level of expression of genes on the nucleotide level, as for example transcriptome analysis, include well-known methods such as RT-PCR, quantitative RT-PCR and nucleic acid microarrays.

By "nucleic acid microarrays" it is herein referred to several different nucleic acid probes attached to a substrate, which can be a microarray, a glass slide, or a bead of microsphere size. The microarray can be made up of polymers, plastics, resins, polysaccharides, silica or a silica-based material, carbon, metals, inorganic glass, or nitrocellulose. The probes can be of nucleic acids such as cDNA ("cDNA microarray") or mRNA ("mRNA microarray") or of oligonucleotides ("oligonucleotide microarray"), said oligonucleotides being able typically to have a length of between about 25 and 60 nucleotides. To determine the expression profile of a particular gene, a nucleic acid corresponding to all or part of said gene is marked, then brought in contact with the microarray under hybridization conditions, leading to the formation of complexes between said marked target nucleic acid and the probes attached to the surface of the microarray which are complementary to this nucleic acid. The presence of marked hybridized complexes is then detected.

Preferentially, the invention is implemented using any current or future method for determining the expression of genes on the basis of the quantity of mRNA in the sample. For example, the skilled person can measure the expression of a gene by hybridization with a labeled nucleic acid probe, such as, for example, by northern blot (for mRNA) or by Southern blot (for cDNA), but also by techniques such as serial analysis of gene expression (SAGE) and derivatives thereof, such as LongSAGE, SuperSAGE, DeepSAGE, etc. It is also possible to use tissue microarrays (TMA5). The tests commonly employed with tissue microarrays comprise immunohistochemistry and fluorescence in situ hybridization. For analysis on the mRNA level, tissue microarrays can be coupled with fluorescence in situ hybridization. Lastly, it is possible to use massive parallel sequencing to determine the quantity of mRNA in the sample (RNA sequencing or whole transcriptome shotgun sequencing). To that end, several methods of massive parallel sequencing are available. Such methods are disclosed in, for example, U.S. Pat. No. 4,882,127, U.S. Pat. No. 4,849,077; U.S. Pat. No. 7,556,922; U.S. Pat. No. 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure Et Ji, Nat Biotechnol., 26(10): 1135-45. 2008; Pihlak et al., Nat Biotechnol., 26(6): 676-684, 2008; Fuller et al., Nature Biotechnol., 27(11): 1013-1023, 2009; Mardis, Genome Med., 1(4): 40, 2009; Metzker, Nature Rev. Genet., 11(1): 31-46, 2010.

When the biological marker is a gene, and the level of expression of the marker is measured at the peptide level, i.e., by measuring the quantity of gene product in its peptide form, any method for determining the level of expression of a polypeptide known to the skilled person may be used. Methods for determining the level of expression of a polypeptide include, for example, mass spectrometry, biochemical tests, including immunological tests such as, for example, traditional immunological detection tests (ELISAs and ELISPOT assays), or such as, for example, immunological tests employing techniques involving transfer of proteins on a support, such as the slot blot (also called dot blot) or the western blot. It is possible, for example, to employ protein microarrays, antibody microarrays or tissue microarrays coupled with immunohistochemistry. Among other techniques that can be used are BRET or FRET techniques, methods of microscopy or histochemistry, including in particular methods of confocal microscopy and electron microscopy, methods based on the use of one or more excitation wavelengths and a suitable optical method, such as an electrochemical method (voltammetry and amperometry), atomic force microscopy, and methods of radio frequency, such as multipolar resonance spectroscopy, confocal and non-confocal, detection of fluorescence, luminescence, chemiluminescence, absorbance, reflectance, transmittance, and birefringence or refraction index (for example, by surface plasmon resonance, by ellipsometry, by a resonant mirror method, etc.), flow cytometry, by radioisotope or magnetic resonance imaging, analysis by polyacrylamide gel electrophoresis (SDS-PAGE); by HPLC-mass spectrophotometry, by liquid chromatography/mass spectrophotometry/mass spectrometry (LC-MS/MS). All these techniques are well-known to the skilled person and it is not necessary to detail them herein.

According to a preferred embodiment, the level of expression of the marker selected from desmoglein 1, involucrin or filaggrin in its peptide form is measured by ELISA. An example of an antibody that can be used for an ELISA adapted to measurement of the level of expression of desmoglein 1 at the peptide level is the rabbit polyclonal antibody against desmoglein marketed by Abcam (item number ab14417). An example of an antibody that can be used for an ELISA adapted to measurement of the level of expression of involucrin at the peptide level is the mouse monoclonal antibody against involucrin marketed by Sigma (item number I9018). An example of an antibody that can be used for an ELISA adapted to measurement of the level of expression of filaggrin at the peptide level is the rabbit polyclonal antibody against filaggrin marketed by Abcam (item number ab81468).

When the biological marker is a lipid, a sugar or a metabolite, the skilled person may to use any method of measurement allowing the assay of said marker in the sample from the subject. These methods include, for example, mass spectrometry and biochemical tests. According to a preferred embodiment, the level of expression of hyaluronic acid is measured by competitive ELISA. Competitive ELISA of hyaluronic acid is a competitive assay which uses a protein binding specifically to labeled hyaluronic acid (biotinylated, for example), i.e., able to bind with hyaluronic acid with high affinity, and microplates coated with hyaluronic acid. The labeled binding protein binds to the immobilized hyaluronic acid, if it is not saturated with free hyaluronic acid contained in the sample. During the following incubation, a conjugate capable of binding to the label of the labeled protein (for example, a conjugate coupled with streptavidin peroxidase) binds to the labeled binding protein. The substrate's reaction is measured by intensity of color, which is inversely proportional to the amount of hyaluronic acid contained in the samples. An example of a protein binding specifically to hyaluronic acid ("HA detector") and of antibodies that can be used for a competitive ELISA adapted to measurement of the level of expression of hyaluronic acid are those of the Tebu kit (item number K-1200-0001). The lipids, in particular ceramides, could for example be assayed by conventional methods for measuring the incorporation of radiolabeled acetate in keratinocytes, or reconstructed skin, or skin explants.

By "reference skin cell sample", it is herein referred to any sample containing human skin cells used as a reference sample. The skilled person can select the reference skin cell sample depending on, for example, the age, sex or skin color of the subject tested. Preferably, according to the invention, the reference skin cell sample is a sample of skin cells from a child. In particularly preferred manner, the reference skin cell sample is a sample of skin cells from a child 2 years of age or older, from a nursing infant or from a newborn.

The skilled person can further choose as a reference skin cell sample a sample of cells not having been treated, or having been irradiated, for example by UV rays. Preferentially, when the biological marker according to the invention is claudin 1, or when the combination of biological markers of the invention comprises claudin 1, the reference skin cell sample is a sample of cells having been irradiated by UV rays.

According to a particular embodiment, the reference skin cell sample according to the invention is a sample from said subject of skin cells not having been treated with said active ingredient.

Alternatively, according to another particular embodiment, the reference skin cell sample according to the invention is a sample of skin cells from a subject presenting said deficiency of the skin barrier, said subject not having been treated for said deficiency.

According to a particular embodiment, the reference skin cell sample according to the invention is a sample of skin cells from a healthy subject.

The skilled person will easily understand that the comparison of step c) is preferably carried out between measurements of levels of expression obtained for skin cell samples of similar size, volume or weight. Thus, it is preferable that the size, and/or the volume and/or the weight of the sample of step a) do not differ by more than 5% from the size, and/or the volume and/or the weight of the sample of step b). Still more preferentially, the size, and the volume and the weight of the sample of step a) do not differ by more than 5% from the size, the volume or the weight of the sample of step b). Alternatively, if the samples of steps a) and b) differ by more than 5% in size, and/or in volume and/or in weight, the skilled person can normalize the levels obtained in steps a) and b) using a normalization factor. This factor could be, for example, a directly accessible physical marker such as the mass of cells of the sample, or the mass of a cellular component, such as the mass of cellular DNA or the mass of cellular proteins.

It can also be advantageous to use as a normalization factor the level of expression of a gene which is expressed to the same degree in all or nearly all of cells of the organism. In other words, according to a particular embodiment of the present invention, the level of expression of a housekeeping gene is used as a normalization factor. According to another embodiment, the levels of steps a) and b) are normalized using the level of expression, not of housekeeping genes, but of proteins encoded thereby. A housekeeping gene is a gene expressed in all cell types, which encodes a protein having a basic function required for the survival of all cell types. A list of human housekeeping genes can be found in Eisenberg et al. (*Trends in Genetics* 19: 362-365, 2003). Housekeeping genes according to the invention include, for example, the following genes: B2M, TFRC, YWHAZ, RPLO, 18S, GUSB, UBC, TBP, GAPDH, PPIA, POLR2A, ACTB, PGK1, HPRT1, IPO8 and HMBS.

The skilled person will thus easily be able to assess the effectiveness of the active ingredient of the invention based on the comparison of step c).

For example, when the level of desmoglein 1, involucrin, filaggrin, claudin 1 and/or hyaluronic acid, in particular in their peptide form, measured in step a), is greater than or equal to the level measured in step b) wherein said reference skin cell sample is a sample of skin cells from a healthy subject, preferably a sample of skin cells from a child, from a child 2 years of age or older, from a nursing infant or a newborn, then the active ingredient is effective in the prevention and/or treatment of at least one deficiency of the skin barrier of a subject.

Similarly, for example, when the level of desmoglein 1, involucrin, ceramide 1, filaggrin, PAD1, hyaluronic acid, transglutaminase 1 and/or claudin 1, measured in step a), is greater than the level of the same marker measured in step b) wherein said reference skin cell sample is a sample from said subject of skin cells not having been treated with said active ingredient, or from a subject presenting said deficiency of the skin barrier and not having been treated for said deficiency, then the active ingredient is effective in the prevention and/or treatment of at least one deficiency of the skin barrier of a subject.

For example, when the level of desmoglein 1, involucrin, ceramide 1, filaggrin, PAD1, hyaluronic acid, transglutaminase 1 and/or claudin 1, measured in step a), is lower than or equal to the level of the same marker measured in step b) wherein said reference skin cell sample is a sample from said subject of skin cells not having been treated with said active ingredient, or from a subject presenting said deficiency of the skin barrier and not having been treated for said deficiency, then the active ingredient is not effective in the prevention and/or treatment of at least one deficiency of the skin barrier of a subject.

By "deficiency of the skin barrier" it is herein referred to one or more physiological or pathological changes in the skin barrier, more particularly one or more physiological or pathological changes in the structure and/or function of the

*stratum corneum* and/or the *stratum granulosum*, in comparison with the normal skin of an adult subject.

In the context of the present application, the deficiency of the skin barrier can be due to a physiological change in the skin barrier.

The skin of children, for example, even when it is healthy, can present a barrier that is not fully functional compared to the skin of an adult. Indeed, the maturation of the skin of a child is accompanied by the development of its barrier function. Similarly, the skin of aged subjects also presents changes in the skin barrier, in comparison with the normal skin of adults, due to its senescence. In the context of the present application, the skin of children and the skin of aged subjects have at least one deficiency of the skin barrier. The immaturity of children's skin and the senescence of the skin of aged subjects are regarded as deficiencies of the skin barrier in the context of the present application.

Moreover, the deficiency of the skin barrier can be due to a pathological change in the skin barrier.

For example, skin damaged by external factors such as climatic conditions, pollution, wounds (cuts or burns, for example) or chemical irritation presents deterioration of the skin barrier.

Furthermore, certain dermatological pathologies are associated with weakening of the skin barrier, such as, for example, baby acne, adolescent acne, rosacea or erythrocouperosis, psoriasis, diaper dermatitis, atopic dermatitis, eczema, contact dermatitis, irritant dermatitis and in particular irritant diaper dermatitis or diaper rash, allergic dermatitis, seborrheic dermatitis, dry skin, skin hyperreactivity.

Preferentially, the deficiency of the skin barrier is selected from baby acne, adolescent acne, rosacea or erythrocouperosis, psoriasis, diaper dermatitis, atopic dermatitis, eczema, contact dermatitis, irritant dermatitis and in particular irritant diaper dermatitis or diaper rash, allergic dermatitis, seborrheic dermatitis, sensitive skin, reactive skin, xerosis, dehydrated skin, skin damaged by the sun, by radiation, by wind, by cold, by heat, by stress, by pollution, cutaneous erythema, aged or photoaged skin, photosensitive skin, scurf, ichthyoses, chapping, burns, sunburns, inflammations due to rays of all kinds, irritations by chemical, physical, bacteriological, fungal or viral, or parasitic agents.

The method of the invention makes it possible to assess the effectiveness of an active ingredient selected from C7 sugars and derivatives of formula (I),

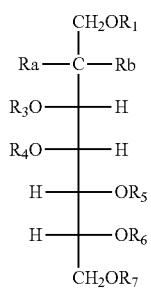

where
Ra hydrogen and Rb is —OR2 or CRaRb is the CO radical;
R1, R2, R3, R4, R5, R6 and R7 are, independently from each other:
hydrogen or a —(CO)—R radical wherein R is a saturated or unsaturated hydrocarbon chain containing from 11 to 24 carbon atoms, optionally substituted by one or more substituents selected from the group consisting of hydroxyl radicals (—OH), ethoxy radicals (—OC2H5) and the —SO3M group with M being hydrogen, an ammonium ion (NH4+) or a metal ion; or a —(CO)—R' radical wherein R' is a saturated or unsaturated hydrocarbon chain containing from 2 to 10 carbon atoms, optionally substituted by one or more substituents selected from the group consisting of hydroxyl radicals (—OH), ethoxy radicals (—OC2H5) and the —SO3M group with M being hydrogen, an ammonium ion (NH4+) or a metal ion.

According to a particular embodiment of the invention, the active ingredient is D-mannoheptulose, of general formula (II)

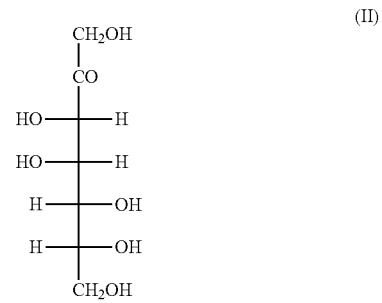

According to another particular embodiment of the invention, the active ingredient is perseitol, of general formula (III)

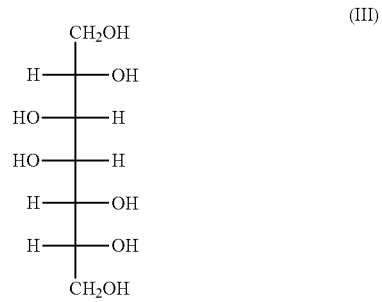

The source of C7 sugars, in particular of D-mannoheptulose and/or perseitol, can be a water-soluble extract of sugars from avocado or from another plant. Aside from that, D-mannoheptulose and perseitol are available commercially (synthetic origin). According to an advantageous variant of the invention, the source of D-mannoheptulose and/or perseitol is a water-soluble extract of avocado sugars.

The water-soluble extract of avocado sugars can be obtained directly from any part of the avocado or the avocado tree, such as the fruit, the skin, the pit, the leaf or the roots of the avocado tree. It is also possible to obtain a water-soluble extract of sugars from the by-products of the avocado processing industry, among which non-exhaustive mention may be made of: fresh avocado pulp, frozen, dehydrated pulp, avocado oil cakes arising from oil extraction processes (mechanical and/or solvent extraction of fruit dehydrated beforehand), de-oiled solid matter arising from wet oil extraction processes (so-called centrifugation process), de-oiled solid matter arising from enzymatic processes for extracting avocado oil, raw avocado purees (guacamole), solid waste arising from units producing these purees. The extract is advantageously obtained from the fresh fruit of the avocado tree. The fruits may be selected from the varieties Hass, Fuerte, Ettinger, Bacon, Nabal, Anaheim, Lula, Reed, Zutano, Queen, Criola Selva, Mexicana Canta, Region Dschang, Hall, Booth, Peterson, Collinson Redn, more advantageously from the varieties Hass, Fuerte and Reed. Preferably, the varieties Hass, Fuerte, Ettinger and Bacon, and more advantageously the varieties Hass and Fuerte, will be selected.

In order to obtain C7 sugars, in particular D-mannoheptulose and/or perseitol, any method for obtaining sugar extracts from plants known to the skilled person could be used. The skilled person will be able to refer in particular to the method disclosed in application FR 2 843 027.

According to an embodiment of the invention, the C7 sugars, in particular the D-mannoheptulose and the perseitol, are at least partially esterified with a —(CO)—R radical wherein R is a saturated or unsaturated hydrocarbon chain containing from 11 to 24 carbon atoms, optionally substituted by one or more substituents selected from the group consisting of hydroxyl radicals (—OH), ethoxy radicals (—OC2H5) and the —SO3M group with M being a hydrogen atom, an ammonium ion (NH4+) or a metal ion. In particular, the C7 sugars are at least partially esterified with a fatty acid residue. The hydrocarbon chain can be linear or branched; it is advantageously linear.

It will be obvious to the skilled person that the active ingredients can be formulated, for example, in order to facilitate their administration. According to an embodiment of the invention, the active ingredient is formulated as a composition, preferentially suitable for topical application.

The composition may further comprise at least one other active compound in addition to C7 sugars and derivatives of formula (I). This other compound may be selected from all of the compounds, and the functional equivalents thereof, stated below:

This other compound may be selected in particular from active ingredients traditionally used in dermatology or cosmetics such as emollients, hydrating active ingredients, keratin synthesis activators, keratoregulators, keratolytics, agents that repair the skin barrier, peroxisome proliferator-activated receptor (PPAR) agonists, RXR or LXR agonists, healing agents, sebum-regulating agents, anti-irritant agents, soothing agents, anti-inflammatory agents, antioxidant agents and anti-aging agents, depigmenting or hypodepigmenting agents, pigmenting agents, lipolytic agents or lipogenesis inhibitors or anti-cellulite or reducing agents, inorganic or organic sun filters and screens, antifungal compounds, preservatives, antibacterial agents, prebiotics and probiotics, antibiotics, immunomodulators.

The invention is particularly useful for monitoring changes in subjects, according to the treatment administered, and can thus be used by the skilled person to best choose the treatment to be administered to the subject.

The second subject-matter of the invention is a method for adapting the treatment of a subject, said treatment comprising an active ingredient selected from C7 sugars and derivatives of formula (I),

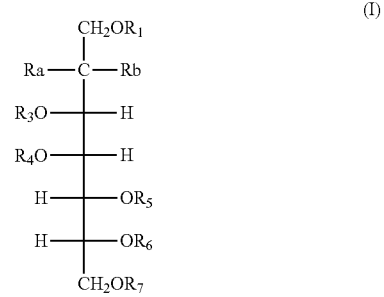

where
Ra is hydrogen and Rb is —OR2 or CRaRb is the CO radical;
R1, R2, R3, R4, R5, R6 and R7 are, independently from each other:
hydrogen or
a —(CO)—R radical wherein R is a saturated or unsaturated hydrocarbon chain containing from 11 to 24 carbon atoms, optionally substituted by one or more substituents selected from the group consisting of hydroxyl radicals (—OH), ethoxy radicals (—OC2H5) and the —SO3M group with M being hydrogen, an ammonium ion (NH4+) or a metal ion; or
a —(CO)—R' radical wherein R' is a saturated or unsaturated hydrocarbon chain containing from 2 to 10 carbon atoms, optionally substituted by one or more substituents selected from the group consisting of hydroxyl radicals (—OH), ethoxy radicals (—OC2H5) and the —SO3M group with M being hydrogen, an ammonium ion (NH4+) or a metal ion;
said method comprising the steps of:
a) assessing the effectiveness of said active ingredient by a method for assessinging the effectiveness of an active ingredient according to the invention;
b) adapting said treatment based on the results obtained in step a).

The skilled person will easily understand that the method of the invention for adapting the treatment of a subject may be implemented for the various active ingredients mentioned above, as well as for compositions comprising same.

According to a particular embodiment of the invention, the active ingredient is D-mannoheptulose, of general formula (II)

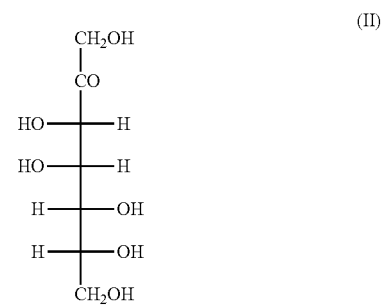

According to another particular embodiment of the invention, the active ingredient is perseitol, of general formula (III)

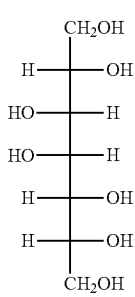

(III)

The skilled person will easily be able to adapt said treatment based on the results obtained in step a).

For example, if the assessment of step a) shows that the active ingredient is not effective in the treatment and/or prevention of at least one barrier deficiency, the skilled person may consequently increase the quantities of active ingredient administered, the concentration of active ingredient or the frequency of administrations. Alternatively, the skilled person may, for example, adapt the treatment by adding other active ingredients complementary to avocado perseose.

If, on the other hand, the active ingredient is effective, as determined in step a, in the treatment and/or prevention of at least one barrier deficiency, the skilled person may, for example, continue the treatment without modifying the quantities of active ingredient administered, the concentration of the active ingredient or the frequency of the administrations, to decrease the quantities of active ingredient administered, the concentration of active ingredient or the frequency of the administrations, or to discontinue the treatment.

The method of the invention thus constitutes a practical tool and a decision-making aid for the skilled person.

The third aspect of the invention relates to a kit for implementing a method according to one of claims 1 to 11, comprising the means needed to measure the level of expression and/or activation of at least one biological marker selected from desmoglein 1, involucrin, ceramides, in particular from ceramides 1 to 9, even more particularly ceramide 1, filaggrin, PAD1, hyaluronic acid, transglutaminase 1, and claudins, in particular claudin 1.

According to a particular embodiment, the kit according to the invention comprises the means needed to measure the level of expression and/or activation of each biological marker of the combination consisting of desmoglein 1, involucrin, ceramide 1, filaggrin, PAD1, hyaluronic acid, transglutaminase 1 and claudin 1.

Preferentially, the means needed to measure the level of expression of desmoglein 1, involucrin, filaggrin, claudin 1 or hyaluronic acid are specific antibodies of said markers. Preferentially, the means needed to measure the level of expression of PAD1 comprise nucleic probes and/or amplification primers capable of binding with PAD1 in its nucleotide form.

FIGURES LEGENDS

FIG. 1: Expression levels of the marker involucrin in normal human keratinocytes, with or without treatment with avocado perseose (perseose).

Figure 2:
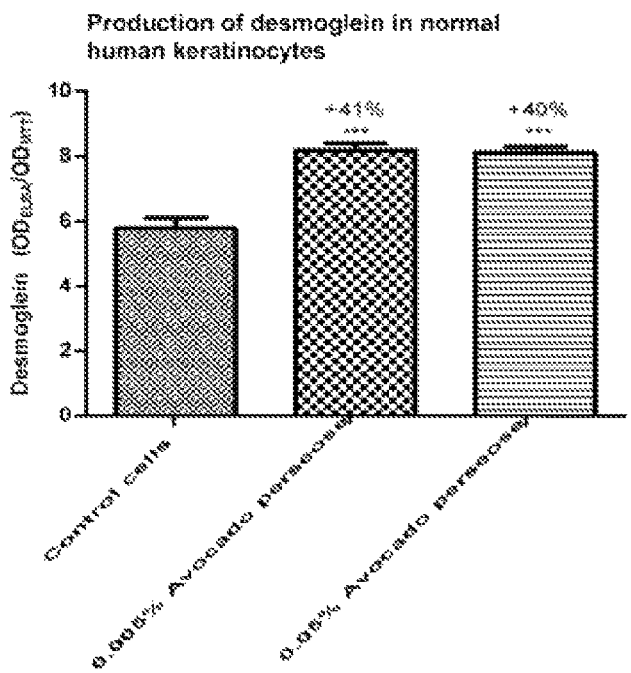

FIG. 2: Expression levels of the marker desmoglein in normal human keratinocytes, with or without treatment with avocado perseose (perseose).

Figure 3:
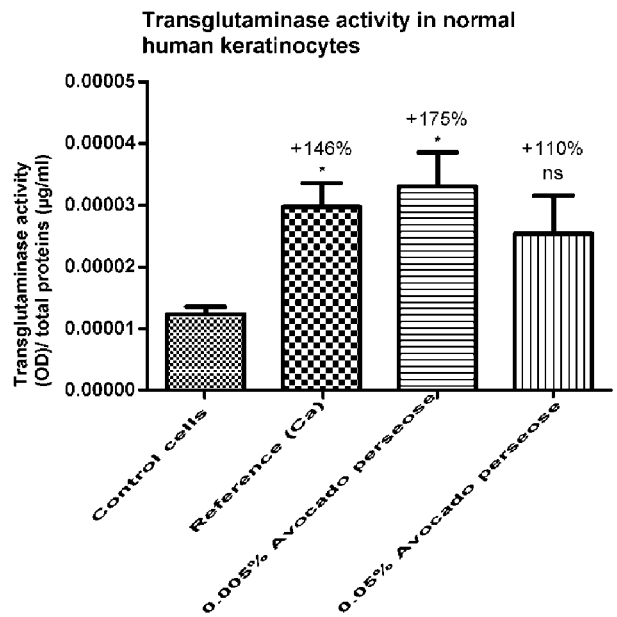

FIG. 3: Activity levels of the marker transglutaminase in normal human keratinocytes, with or without treatment with avocado perseose.

Figure 4:
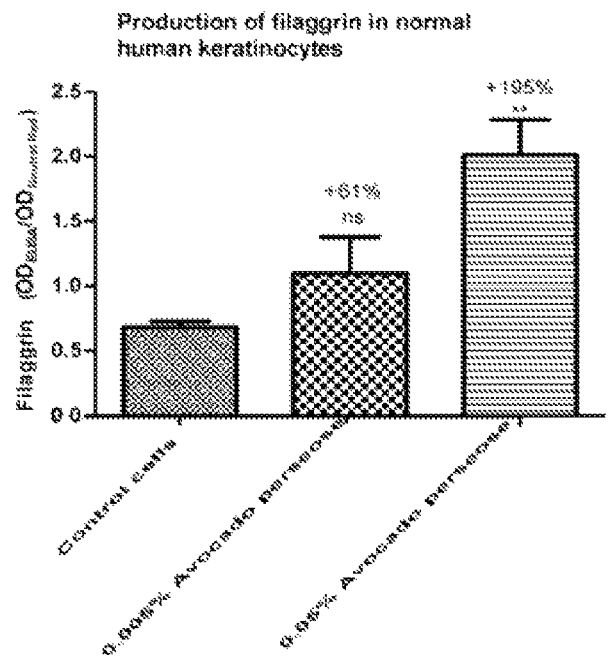

FIG. 4: Expression levels of the marker filaggrin in normal human keratinocytes, with or without treatment with avocado perseose.

Figure 5:
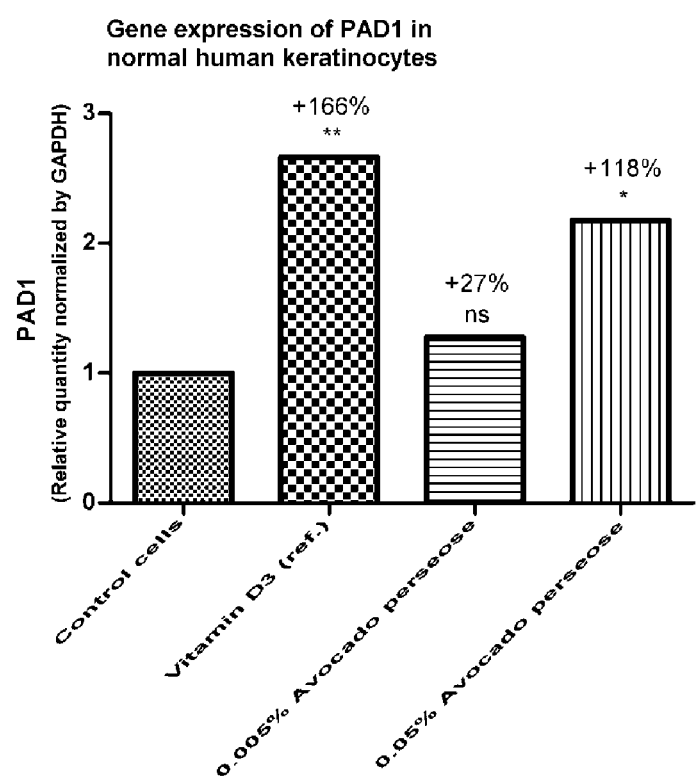

FIG. 5: Expression levels of the marker PAD1 in normal human keratinocytes, with or without treatment with avocado perseose.

Figure 6:
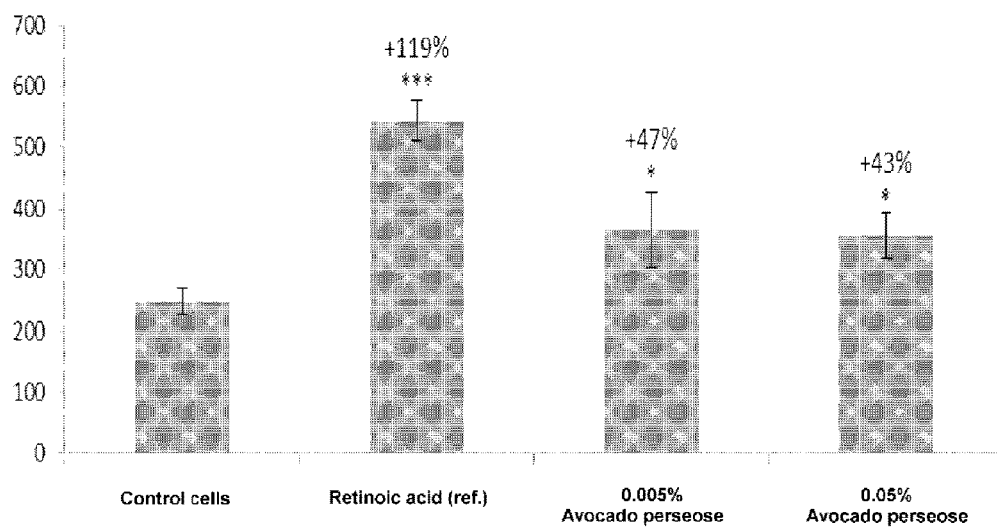

FIG. 6: Expression levels of the marker hyaluronic acid in normal human keratinocytes, with or without treatment with avocado perseose.

The following examples illustrate the invention but are not limiting.

EXAMPLES

1. Example 1: Preparation of a Water-Soluble Extract of Avocado Sugars

Fresh avocados, Hass variety, are cut into thin slices 2 to 5 mm in thickness, pit included, using a disc slicer. The drying tool is a temperature-controlled hot airflow drying chamber. The sliced avocados are distributed in a thickness of 4 to 5 cm on tiered wire racks. The drying temperature set to 80° C. and its duration is 48 hours. Once dried, the fruits are subjected to cold pressing. This operation is carried out on a small Komet laboratory press. Oil and oil cake are thus obtained.

The oil cake is crushed and then extracted in the presence of 70% ethanol or water.

The liquid and solid portions are separated by centrifugation, for example. The soluble (liquid) fraction is collected to be purified and concentrated according to the following procedure:

- Demineralization using ion-exchange resins: demineralization of heptuloses by passing over OH− resins, then over H+ resin.
- 10,000 Da ultrafiltration: the ultrafiltration is carried out with a system equipped with four 10 kDa cutoff membranes.
- Vacuum concentration: the purified extract is concentrated using a vacuum evaporator until a dry matter of near 4% is obtained.
- Packaging: the concentration of the extract is adjusted to 5% dry matter, preservative is added, and then it undergoes sterile filtration with a 0.2 μm cutoff membrane and is packaged.

Table 1 gives the composition of the extract of avocado C7 sugars, at 5% dry matter, prepared according to the method described above:

TABLE 1

| Appearance | Solution, pale yellow in color |
|---|---|
| Analytical criteria | |
| Dry matter | 5% |
| pH (¼ dilution) | 7.0 |
| Composition (%/dry matter) | |
| Sucrose | 3.0 |
| Glucose | 7.5 |
| D-Mannoheptulose | 40.0 |
| Fructose | 8.6 |
| Perseitol | 40.0 |

According to this same method, two other extracts were prepared, the pH, absorbance and C7 sugar content of which are given in Table 2. C7 sugar content corresponds to the sum of perseitol and D-mannoheptulose analyzed by HPLC.

TABLE 2

|  | Batch | |
| --- | --- | --- |
|  | 1 | 2 |
| Dry matter | 5% | 5% |
| pH (¼ dilution) | 5.9 | 5.4 |
| C7 sugars/dry matter | 80.5 | 83.4 |

Avocado sugars prepared by the method of Example 1 and called "avocado perseose" below can be used in various formulations.

Exemplary Formulations

Hydrating Cream

TABLE 3

| Raw material/Trade name | % |
| --- | --- |
| CAPRYLO CAPRATE GLYC | 1 to 15% |
| SUNFLOWER OIL SR | 1 to 15% |
| PURE CETYL ALCOHOL | 1 to 5% |
| GLYCERYL STEARATE CITRATE | 1 to 10% |
| BEESWAX | 1 to 5% |
| EUMULGIN SG | 0 to 2% |
| VITAMIN E ACETATE | 0 to 1% |
| PURIFIED WATER | q.s. 100% |
| CARBOPOL ULTREZ 20 | 0 to 1% |
| GLYCEROL | 1 to 10% |
| XANTHAN GUM | 0 to 1% |
| LYE XI | 0 to 1% |
| PRESERVATIVE | 0 to 2% |
| AVOCADO PERSEOSE | 0 to 1% |

Restructuring Milk

TABLE 4

| Raw material/Trade name | % |
| --- | --- |
| PURIFIED WATER | q.s. 100% |
| SUNFLOWER OIL SR | 1 to 10% |
| HYDRO COPRA OIL | 1 to 10% |
| SWEET ALMOND OIL | 1 to 10% |
| CORN OIL | 1 to 10% |
| GLYCEROL MONOSTEARATE | 1 to 10% |
| STEARIC ACID | 1 to 10% |
| PRESERVATIVE | 0 to 2% |
| C16-C18 CETYL ALCOHOL | 0 to 2% |
| VITAMIN E ACETATE | 0 to 1% |
| LYE XI | 0 to 1% |
| AVOCADO PERSEOSE | 0 to 1% |

Cleansing Wash

TABLE 5

| Raw material/Trade name | % |
| --- | --- |
| PURIFIED WATER | q.s. 100% |
| GLYCEROL | 1 to 10% |
| SODIUM COCOYL | 1 to 10% |
| PRESERVATIVE | 0 to 2% |
| RICIN HYDROBUTETH 26 | 0 to 2% |
| ALLANTOINE | 0 to 2% |
| TARTARIC ACID | 0 to 2% |
| ALOE VERA POWDER SR | 0 to 2% |
| SAPONARIA EXTRACT SR | 0 to 2% |
| LYE XI | 0 to 2% |
| AVOCADO PERSEOSE | 0 to 1% |

Shampoo

TABLE 6

| Raw material/Trade name | from |
| --- | --- |
| PURIFIED WATER | q.s. 100% |
| COCAMIDO PROPYL BETAINE | 1 to 10% |
| GLYCEROL | 1 to 10% |
| COCOGLUCOSIDE XI | 1 to 10% |
| SODIUM MYRETH SULFATE | 1 to 10% |
| PRESERVATIVE | 0 to 2% |
| DISTEARATE PEG 6000 | 0 to 2% |
| POLYQUARTERNIUM JR400 XI | 0 to 2% |
| DEXTROROTATORY PANTHENOL | 0 to 2% |
| CITRIC ACID HYD XI | 0 to 2% |
| AVOCADO PERSEOSE | 0 to 1% |

SPF 50+ Sun Lotion

TABLE 7

| Raw material/Trade name | from |
| --- | --- |
| COPRA CAPRYLATE/CAPRATE | 5 to 20% |
| DICAPRYLYL CARBONATE | 5 to 20% |
| CAPRYLOCAPRATE GLYC | 5 to 20% |
| MIGLYOL GEL B | 5 to 20% |
| TITANIUM DIOXIDE JOJOBA ESTERS | 1 to 15% |
| TINOSORB S | 1 to 5% |
| DIETAMIN HYDBENZO YHEXBENZ | 1 to 10% |
| ETHYL HEXYL TRIAZONE | 1 to 10% |
| AVOCADO OIL HAREF | 1 to 5% |
| ALPHA TOCOPHEROL | 0.05 to 1% |
| LAURYL GLUCOSE-GLYSTEARATE XI | 2 to 12% |
| PURIFIED WATER | q.s. 100% |
| GLYCEROL | 1 to 10% |
| XANTHAN GUM | 0 to 1% |
| PRESERVATIVE | 0 to 2% |
| POTASSIUM CETYL PHOSPHATE | 0 to 2% |
| LYE XI | 0 to 2% |
| PHENYLBENZIMIDAZO SULFON AC | 1 to 5% |
| AVOCADO PERSEOSE | 0 to 1% |

Avocado sugars prepared by the method of Example 1 and called "avocado perseose" below were used to study the expression of markers of the barrier function under various conditions.

2. Epidermal Maturation a. Expression of Involucrin

Materials and Methods:

Normal human epidermal keratinocytes were incubated in the presence of 0.005% and 0.05% (w/v) avocado perseose for 48 hours.

At the end of the treatment, the involucrin produced was assayed on the surface of keratinocytes by means of a cell-based ELISA. The amount of involucrin was related to the number of living cells estimated by means of an MTT assay.

Results: the results are illustrated in Table 8 below and in FIG. 1.

0.005% and 0.05% avocado perseose significantly stimulated the expression of involucrin in normal human keratinocytes: respectively +17%, $p<0.01$ and +56%, $p<0.001$.

TABLE 8

| | Involucrin ($OD_{ELISA}/OD_{MTT}$) | |
|---|---|---|
| Control cells | 2.245 ± 0.068 | |
| 0.005% Avocado perseose | 2.633 ± 0.051 | +17% ** |
| 0.05% Avocado perseose | 3.509 ± 0.178 | +56% *** |

** $p < 0.01$;
*** $p < 0.001$ versus control cells, one-way analysis of variance followed by Dunnett's test (GraphPad PRISM software)

b. Expression of Desmoglein

Materials and Methods:

Normal human epidermal keratinocytes were grown in differentiation-inducing medium (supplemented with Ca++) and incubated in the presence of 0.005% and 0.05% avocado perseose for 48 hours.

At the end of the treatment, the desmoglein-1 produced was assayed on the surface of keratinocytes with a cell-based ELISA. The amount of desmoglein was related to the number of living cells estimated by means of an MTT assay.

Results: the results are illustrated in Table 9 below and in FIG. 2.

0.005% and 0.05% avocado perseose significantly stimulated the expression of desmoglein 1 in differentiated normal human keratinocytes: respectively +41%, $p<0.001$ and +40%, $p<0.001$.

TABLE 9

| | Desmoglein ($OD_{ELISA}/OD_{MTT}$) | |
|---|---|---|
| Control cells | 5.791 ± 0.641 | |
| 0.005% Avocado perseose | 8.182 ± 0.430 | +41% *** |
| 0.05% Avocado perseose | 8.094 ± 0.395 | +40% *** |

*** $p < 0.001$ versus control cells, one-way analysis of variance followed by Dunnett's test (GraphPad PRISM software)

3. Strengthening of the Lipid Barrier: Ceramide Neosynthesis

Materials and Methods:

Reconstructed day-5 epidermises were grown under the following conditions:

Control epidermises: depleted medium,

Differentiated epidermises: complete differentiation medium, 0.005% and 0.05% (DM) avocado perseose in depleted medium.

After 24 hours of incubation, the culture medium was changed and supplemented with radiolabeled acetate (14C-acetate). The epidermises were then incubated again for 48 hours.

At the end of the treatment, neosynthesized ceramides were analyzed by quantification of the radioactivity incorporated after thin-layer chromatography.

Results: the results are illustrated in Table 10 below.

0.005% and 0.05% avocado perseose increased the synthesis of ceramides in reconstructed human epidermises: respectively +32% and +27%.

TABLE 10

| | Quantity of ceramides | |
|---|---|---|
| | Relative intensity (mean) | % of the control |
| Control epidermises | 14.2 | 100 |
| Differentiated epidermises | 19.7 | 138 |
| 0.005% Avocado perseose | 18.0 | 132 |
| 0.05% Avocado perseose | 18.7 | 127 |

4. Water Regulation a. Enzymatic Activity of Transglutaminase

Materials and Methods:

Normal human epidermal keratinocytes were incubated in the presence of 0.005% and 0.05% avocado perseose in KGM Gold (Lonza) keratinocyte growth medium; a control consisting of cells cultured in pro-differentiating medium (KGM Gold supplemented with Ca++) was prepared in parallel.

After 72 hours of incubation, the cells were lysed and the activity of intracellular transglutaminase assayed using the Transglutaminase Colorimetric Microassay Kit (Covalab). The results were normalized relative to the amount of total proteins determined using the BC Assay Kit (Interchim).

Results: the results are illustrated in Table 11 below and in FIG. 3.

0.005% avocado perseose significantly stimulated the enzymatic activity of transglutaminase in normal human epidermal keratinocytes: +175%, $p<0.05$.

TABLE 11

| | Transglutaminase activity (OD/total proteins) | |
|---|---|---|
| Control cells | 0.000012 ± 0.0000018 | |
| Reference (Ca) | 0.00003 ± 0.0000054 | +146% * |
| 0.005% Avocado perseose | 0.000033 ± 0.0000075 | +175% * |
| 0.05% Avocado perseose | 0.000025 ± 0.0000086 | +110% ns |

* $p < 0.05$ versus control cells, one-way analysis of variance followed by Dunnett's test (GraphPad PRISM software)

b. Expression of Filaggrin

Materials and Methods:

Normal human epidermal keratinocytes were incubated in the presence of 0.005% and 0.05% avocado perseose for 72 hours.

At the end of the treatment, the filaggrin produced was assayed on the surface of keratinocytes with a cell-based ELISA. The amount of filaggrin was related to the number of living cells estimated by means of a neutral red assay.

Results: the results are illustrated in Table 12 below and in FIG. 4.

0.05% avocado perseose significantly stimulated the production of filaggrin by normal human epidermal keratinocytes: +195%, $p<0.01$.

TABLE 12

| | Filaggrin ($OD_{ELISA}/OD_{NR}$) | |
|---|---|---|
| Control cells | 0.683 ± 0.089 | |
| 0.005% Avocado perseose | 1.102 ± 0.681 | +61% ns |
| 0.05% Avocado perseose | 2.014 ± 0.546 | +195% ** |

** $p < 0.01$ versus control cells, one-way analysis of variance followed by Dunnett's test (GraphPad PRISM software).

c. Gene Expression of Peptidylarginine Deiminase (PAD1) Enzyme

Materials and Methods:

Normal human epidermal keratinocytes, cultured in differentiation-inducing medium (supplemented with Ca++), were incubated for 48 hours in the presence of 0.005% and 0.05% avocado perseose or 10-7M vitamin D3 (1α,25-dihydroxyvitamin D3; Sigma), positive reference.

At the conclusion of the treatment, the RNA were extracted and the gene expression of PAD1 was evaluated by RT-PCR; the reference gene GAPDH was used to normalize the results.

Results: the results are illustrated in Table 13 below and in FIG. 5.

0.05% avocado perseose significantly stimulated the gene expression of PAD1: +118%, p<0.05.

TABLE 13

|  | PAD1 (Relative Quantity normalized by GAPDH) | |
| --- | --- | --- |
| Control cells | 1.00 | |
| $10^{-7}$ M Vitamin D3 | 2.66 | +166% ** |
| 0.005% Avocado perseose | 1.27 | +27% ns |
| 0.05% Avocado perseose | 2.18 | +118% * |

\* p < 0.05;
\*\* p < 0.01 versus control cells, one-way analysis of variance followed by Dunnett's test (GraphPad PRISM software)

d. Production of Hyaluronic Acid

Materials and Methods:

Normal human epidermal keratinocytes were incubated in the presence of 0.005% and 0.05% avocado perseose or 10-7 M retinoic acid (all-trans-retinoic acid; Sigma), positive reference.

After 24 hours of incubation, hyaluronic acid produced by the keratinocytes was assayed in the cultured supernatants with an ELISA (Tebu). The quantity of hyaluronic acid measured was related to the number of living cells estimated by means of a neutral red assay.

Results: the results are illustrated in Table 14 below and in FIG. 6.

Avocado perseose significantly increased the quantity of hyaluronic acid produced by normal human keratinocytes: +47%, p<0.05 at 0.005% and +43%, p<0.05 at 0.05%.

TABLE 14

|  | Hyaluronic acid (ng/ml/living cells) | |
| --- | --- | --- |
| Control cells | 248.445 ± 21.248 | |
| $10^{-7}$ M Retinoic acid | 544.024 ± 34.026 | +119% *** |
| 0.005% Avocado perseose | 365.737 ± 61.68 | +47% * |
| 0.05% Avocado perseose | 356.179 ± 37.353 | +43% * |

\* p < 0.05;
\*\*\* p < 0.001 versus control cells, one-way analysis of variance followed by Dunnett's test (GraphPad PRISM software).

5. Model of UV Damage

Certain environmental stresses are harmful to the maturation of the epidermis and in particular the barrier function (Yamamoto T, Kurasawa M, Hattori T, Maeda T, Nakano H, Sasaki H. Relationship between expression of tight junction-related molecules and perturbed epidermal barrier function in UVB-irradiated hairless mice. Arch Dermatol Res 2008; 300: 61-8; Valacchi et al. Cutaneous responses to environmental stressors. Ann NY Acad Sci 2012; 1271: 75-81, 2012).

Materials and Methods:

Normal human epidermal keratinocytes, grown in differentiation-inducing medium (supplemented with Ca++), were preincubated in the presence of 0.001% avocado perseose for 48 hours or 0.005% and 0.05% for 24 hours. The keratinocytes were then irradiated, in PBS, by UVA+B rays at a dose of 36 kJ/m$^2$. The cells were then incubated again for 6 hours in the presence of avocado perseose.

At the conclusion of the treatment, the RNA were extracted and the gene expression of each of claudin 1, filaggrin and involucrin was evaluated RT-PCR. The results were normalized by amplification of a reference gene: β2-microglobulin for the tests using 0.001% avocado perseose or HPRT for the tests using 0.005% and 0.05% avocado perseose.

Results: the results are illustrated in Table 15 below.

UV irradiation induced a significant decrease in the gene expression of the three barrier markers studied.

Avocado perseose made it possible to offset the effect of UV rays by significantly stimulating the gene expression of claudin 1 (+131%, p<0.001 at 0.001% and 32%, p<0.01 at 0.05%), filaggrin (+22%, p<0.05 at 0.005% and +27%, p<0.01 at 0.05%) and involucrin (+191%, p<0.01 at 0.001%) under UV rays.

TABLE 15

|  | Claudin 1 | | Filaggrin | | Involucrin | | | |
| --- | --- | --- | --- | --- | --- | --- | --- | --- |
| Control cells | 1.00 |  | 1.00 |  | 1.00 |  | 1.00 |  |
| Irradiated control UVA + B 36 kJ/m$^2$ | 0.39 | −61% $$$ | 0.50 | −50% $$$ | 0.56 | −44% $$$ | 0.29 | −71% $$$ |
| 0.001% Avocado perseose | 0.90 | +131% *** | / |  | / |  | 0.85 | +191% ** |
| 0.005% Avocado perseose | / |  | 0.60 | +20% ns | 0.69 | +22% * | / |  |
| 0.05% Avocado perseose | / |  | 0.66 | +32% ** | 0.71 | +27% ** | / |  |

$$$ p < 0.001 versus control cells
\* p < 0.05;
\*\* p < 0.01;
\*\*\* p < 0.001 versus irradiated control
One-way analysis of variance followed by Tukey's test (GraphPad PRISM software).

The invention claimed is:

1. A method for assessing effectiveness of an active ingredient selected from C7 sugars and derivatives of formula (I),

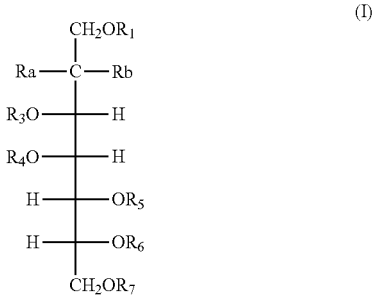

wherein
Ra is hydrogen and Rb is —OR2, or CRaRb is a CO radical;
R1, R2, R3, R4, R5, R6 and R7 are, independently from each other:
hydrogen,
a —(CO)—R radical wherein R is a saturated or unsaturated hydrocarbon chain containing from 11 to 24 carbon atoms, optionally substituted by one or more substituents selected from the group consisting of hydroxyl radicals (—OH), ethoxy radicals (—OC2H5) and —SO3M wherein M is hydrogen, an ammonium ion (NH4+) or a metal ion, or
a —(CO)—R' radical wherein R' is a saturated or unsaturated hydrocarbon chain containing from 2 to 10 carbon atoms, optionally substituted by one or more substituents selected from the group consisting of hydroxyl radicals (—OH), ethoxy radicals (—OC2H5) and —SO3M wherein M is hydrogen, an ammonium ion (NH4+) or a metal ion;
in the prevention and/or treatment of at least one deficiency of the skin barrier of a subject, said method comprising:
a. measuring the level of expression and/or activation of at least one biological marker in a sample of skin cells from the subject, wherein said biological marker is selected from the group consisting of:
markers of epidermal maturation,
markers of the lipid barrier,
markers of water regulation, and
markers of regulation of the *stratum granulosum;*
b. measuring the level of expression and/or activation of said biological marker in a reference skin cell sample;
c. comparing the levels of expression and/or activation obtained in step a) with the levels of expression and/or activation obtained in step b);
d. evaluating the effectiveness of said active ingredient based on the comparison of step b).

2. The method of claim 1, wherein step a) comprises measuring the level of expression and/or activation of a combination of biological markers from a sample of skin cells from the subject, wherein in the combination of markers comprises:
at least one marker of epidermal maturation;
at least one marker of the lipid barrier;
at least one marker of water regulation; and
at least one marker of regulation of the *stratum granulosum*.

3. The method of claim 2, wherein the combination of biological markers consists of desmoglein 1, involucrin, ceramide 1, filaggrin, PAD1, hyaluronic acid, transglutaminase 1 and claudin 1.

4. The method of claim 1, wherein said reference skin cell sample is a sample of skin cells from said subject, said skin cells not having been treated with said active ingredient.

5. The method of claim 1, wherein said reference skin cell sample is a sample of skin cells from a subject presenting said deficiency of the skin harrier, said subject not having been treated for said deficiency.

6. The method of claim 1, wherein said reference skin cell sample is a sample of skin cells from a healthy subject.

7. The method of claim 1, wherein the reference skin cell sample is a sample of skin cells from a child.

8. The method of claim 1, wherein deficiency of the skin barrier is baby acne, adolescent acne, rosacea or erythrocouperosis, psoriasis, diaper dermatitis, atopic dermatitis, eczema, contact dermatitis, irritant dermatitis and in particular irritant diaper dermatitis or diaper rash, allergic dermatitis, seborrheic dermatitis, sensitive skin, reactive skin, xerosis, dry skin, skin damaged by the sun, by radiation, by wind, by cold, by heat, by stress, by pollution, cutaneous erythema, aged or photoaged skin, photosensitive skin, scurf, ichthyoses, chapping, burns, sunburns, inflammations due to rays of all kinds, irritations by chemical, physical, bacteriological, fungal or viral, Of parasitic agents.

9. The method of claim 1, wherein the level of expression of a marker selected from desmoglein 1, involucrin and filaggrin corresponds to the level of expression of said marker in its peptide form, wherein the level of expression of PAD1 or of claudin 1 corresponds to the level of expression of said marker in its nucleotide form.

10. The method of claim 1, wherein said active ingredient is D-mannoheptulose of general formula (II)

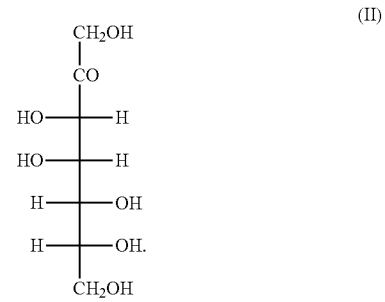

11. The method of claim 1, wherein said active ingredient is perseitol, of general formula (III)

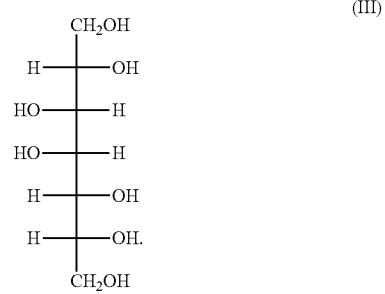

12. The method of claim 1, wherein said active ingredient is in the form of a composition.

13. The method of claim 1, wherein the composition further comprises at least one other active compound in addition to C7 sugars and derivatives of formula (I).

14. The method of claim 1 wherein said marker of epidermal maturation is desmoglein 1 or involucrin.

15. The method of claim 1, wherein said marker of the lipid barrier is selected from ceramides.

16. The method of claim 1, wherein said marker of the lipid barrier is selected from the group consisting of ceramides 0.1 to 9.

17. The method of claim 16, wherein said marker of the lipid bather is ceramide 1.

18. The method of claim 1, wherein said marker of water regulation is selected from the group consisting of filaggrin, PAD1, hyaluronic acid and transglutaminase 1.

19. The method of claim 1, wherein said marker of regulation of the stratum *granulosum* is selected from claudins.

20. The method of claim 19, wherein said marker of regulation of the stratum *granulosum* is claudin 1.

21. The method of claim 7, wherein, said child is selected from the group consisting of infants of less than 1 month, infants between 1 month and 2 years, and children between 2 and 16 years of age.

22. The method of claim 12, wherein said composition is suitable for topical application.

\* \* \* \* \*

UNITED STATES PATENT AND TRADEMARK OFFICE
CERTIFICATE OF CORRECTION

PATENT NO. : 10,175,230 B2
APPLICATION NO. : 14/785212
DATED : January 8, 2019
INVENTOR(S) : Philippe Msika, Caroline Baudouin and Stephanie Bredif Page 1 of 1

It is certified that error appears in the above-identified patent and that said Letters Patent is hereby corrected as shown below:

In the Claims

Column 28, Claim 5, Line 10, please replace "said deficiency of the skin harrier" with -- said deficiency of the skin barrier --.

Column 29, Claim 16, Lines 9 to 10, please replace "consisting of ceramides 0.1 to 9" with -- consisting of ceramides 1 to 9 --.

Column 29, Claim 17, Lines 11 to 12, please replace "said marker of the lipid bather" with -- said marker of the lipid barrier --.

Signed and Sealed this
Third Day of November, 2020

Andrei Iancu
*Director of the United States Patent and Trademark Office*